United States Patent
Azuma et al.

(10) Patent No.: US 7,473,226 B2
(45) Date of Patent: Jan. 6, 2009

(54) ULTRASONOGRAPHIC DEVICE AND ULTRASONOGRAPHIC METHOD

(75) Inventors: Takashi Azuma, Kawasaki (JP); Shin-ichiro Umemura, Muko (JP); Hirotaka Baba, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 202 days.

(21) Appl. No.: 10/562,465

(22) PCT Filed: Jun. 9, 2004

(86) PCT No.: PCT/JP2004/008391

§ 371 (c)(1),
(2), (4) Date: Dec. 27, 2005

(87) PCT Pub. No.: WO2005/013829

PCT Pub. Date: Feb. 17, 2005

(65) Prior Publication Data

US 2006/0173334 A1    Aug. 3, 2006

(30) Foreign Application Priority Data

Aug. 6, 2003    (JP) .............................. 2003-206184

(51) Int. Cl.
*A61B 8/00* (2006.01)
(52) U.S. Cl. ....................... 600/443; 600/437; 600/441; 600/447; 600/455
(58) Field of Classification Search .......... 600/437–457
See application file for complete search history.

(56) References Cited

U.S. PATENT DOCUMENTS 5,582,173 A * 12/1996 Li .............................. 600/443

| 2003/0171668 | A1* | 9/2003 | Tsujino et al. | ............... 600/407 |
|---|---|---|---|---|
| 2004/0068188 | A1* | 4/2004 | Robinson | ..................... 600/447 |
| 2005/0018540 | A1* | 1/2005 | Gilbert et al. | ............... 367/138 |
| 2005/0154304 | A1* | 7/2005 | Robinson | ..................... 600/443 |

FOREIGN PATENT DOCUMENTS

| JP | 2002-526225 | 8/2002 |
|---|---|---|
| JP | 2003-135454 | 5/2003 |

OTHER PUBLICATIONS

Mustafa Karaman et al., "Adaptive Multi-element Synthetic Aperture Imaging with Motion and Phase Aberration Correction", IEEE Transactions on Ultrasonics, Ferroelectrics, and Frequency Control, vol. 45, No. 4, pp. 1077-1087, Jul. 1998.

* cited by examiner

*Primary Examiner*—Brian L. Casler
*Assistant Examiner*—Sanjay Cattungal
(74) *Attorney, Agent, or Firm*—Antonelli, Terry, Stout & Kraus, LLP.

(57) ABSTRACT

In an ultrasonic imaging device having an image synthesizing unit, correlation between images to be synthesized is computed for balancing between an improvement in contrast resolution and an improvement in spatial resolution, and an amount of displacement between the images is computed. When the amount of displacement is large, the signals after envelop detection are synthesized. When the amount of displacement is small, RF signals are synthesized. Alternatively, the mixing frequency may be variable according to the amount of displacement, and the balance between an improvement in spatial resolution and that in contract resolution is achieved according to a degree of the positional displacement.

1 Claim, 10 Drawing Sheets

FIG. 1
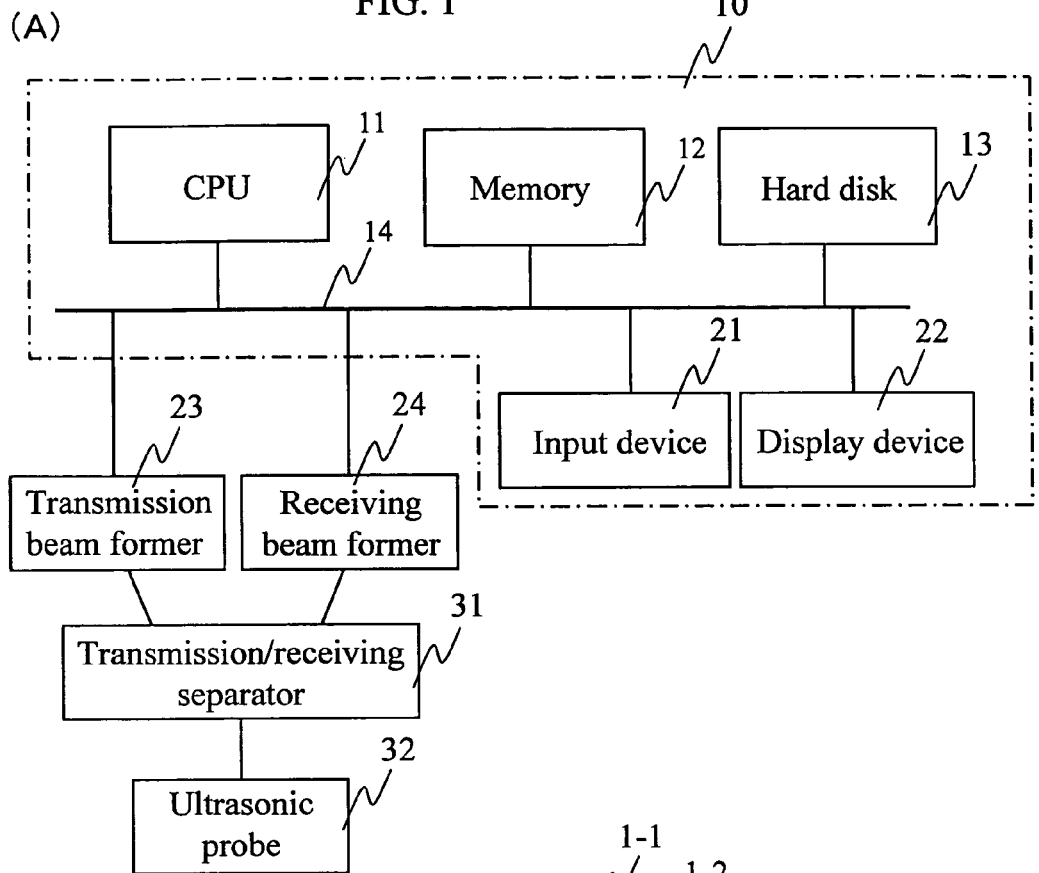
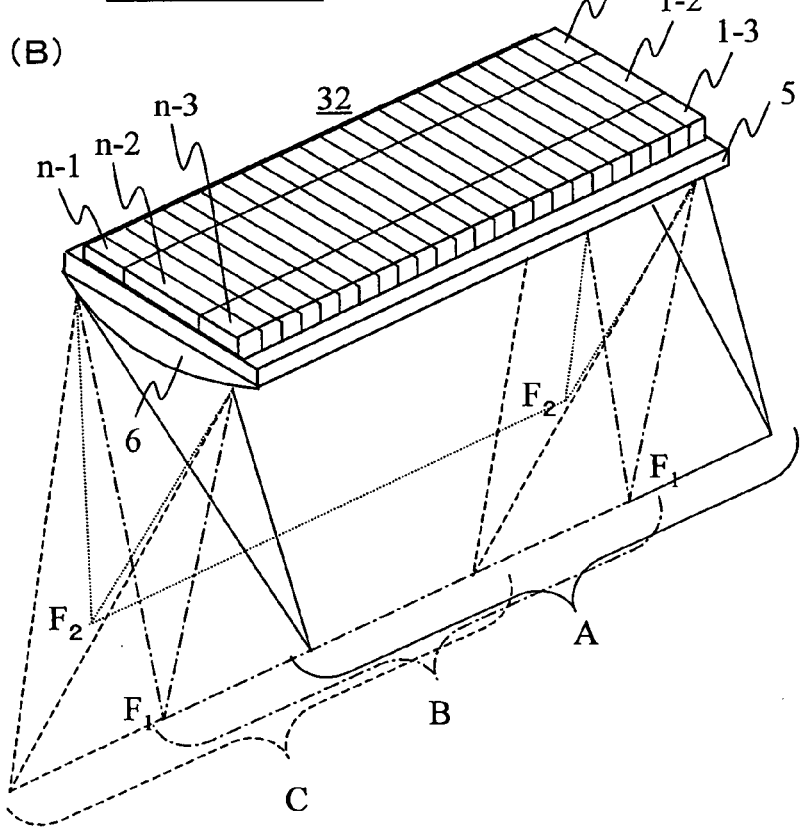

FIG. 6
(A)
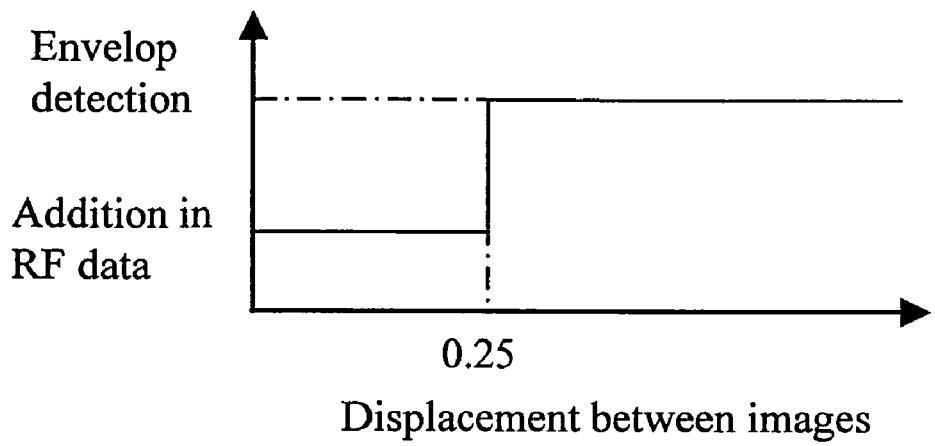
Displacement between images
(B)
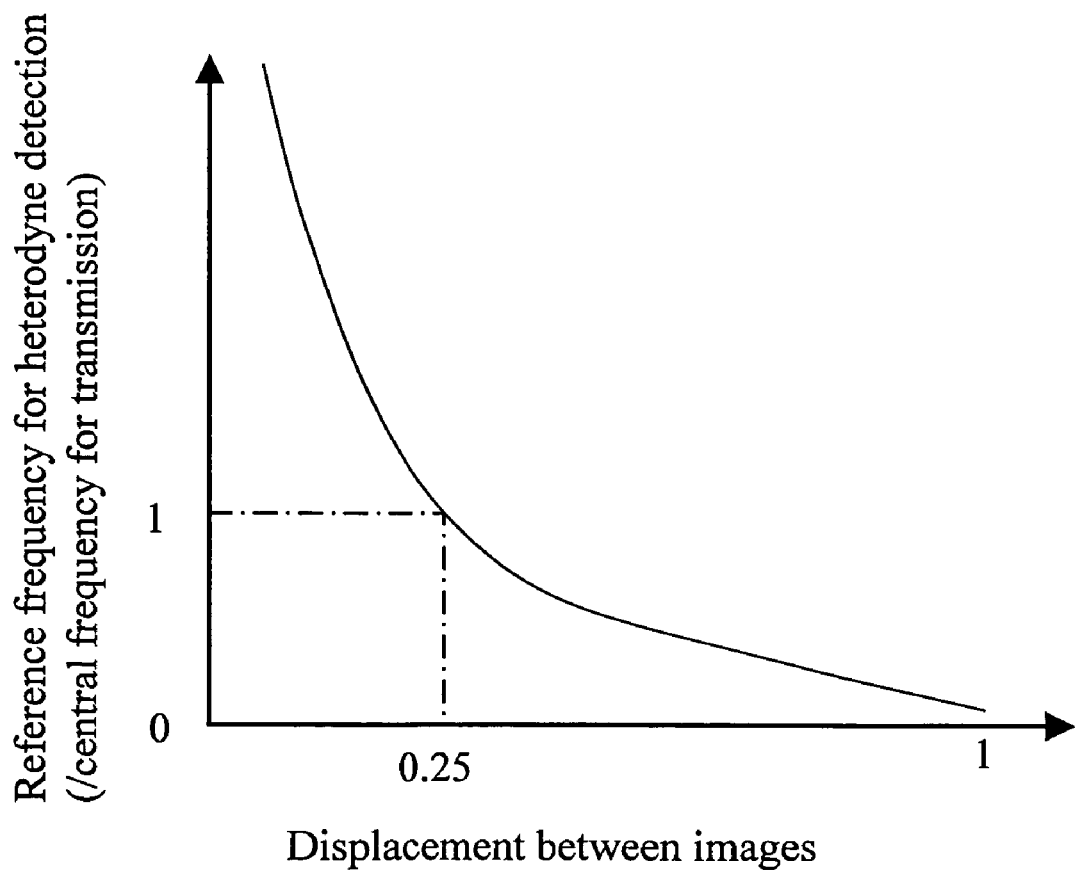
Displacement between images FIG. 7
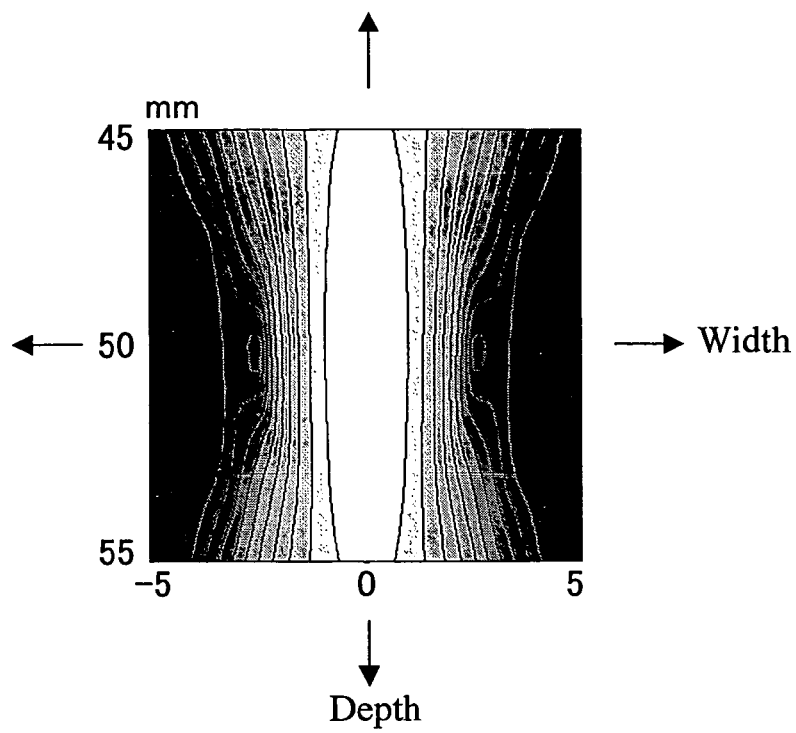
Depth
FIG. 8
(A) No carrier
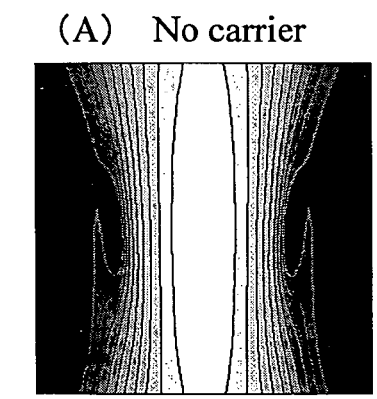
(C) 2 MHz; Real carrier
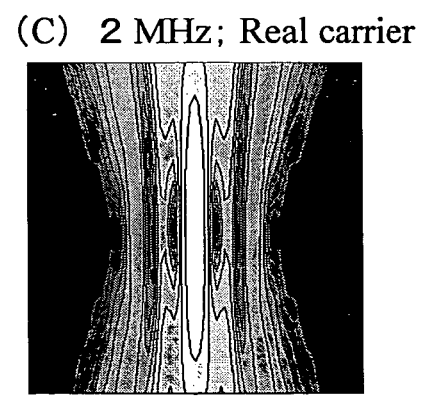
(B) 1 MHz
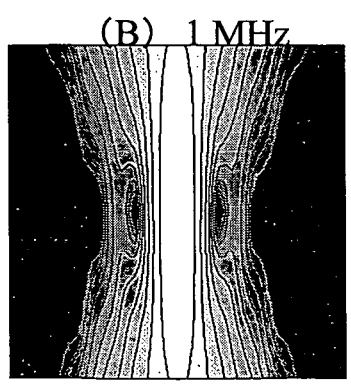
(D) 3 MHz
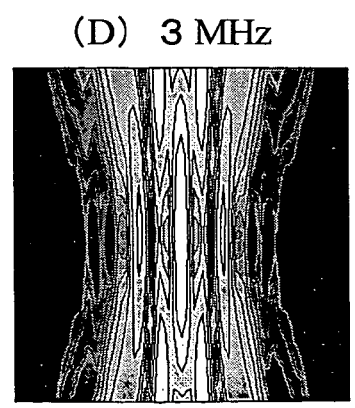

FIG. 9
(A) Addition after envelop detection
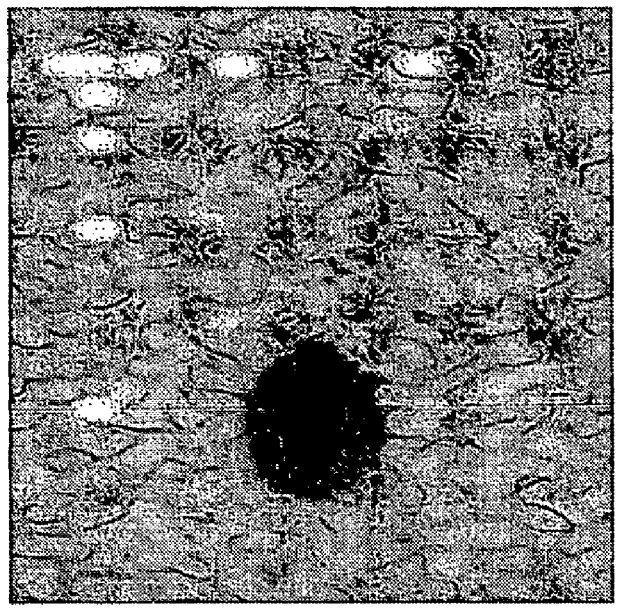
(B) Addition in RF data
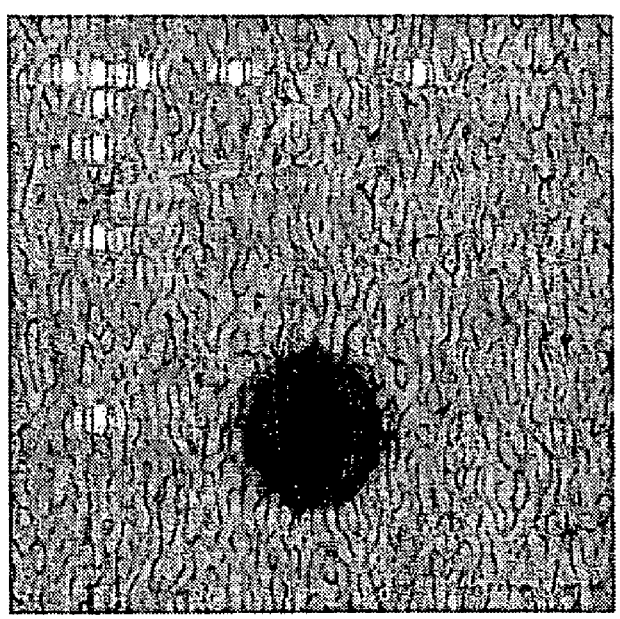

FIG. 10
(A) No carrier
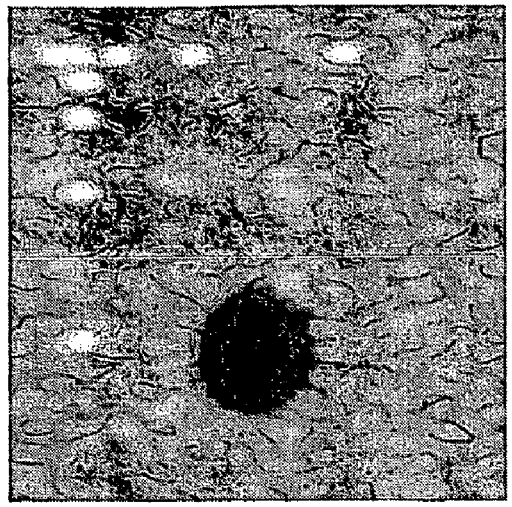
(B) 1 MHz
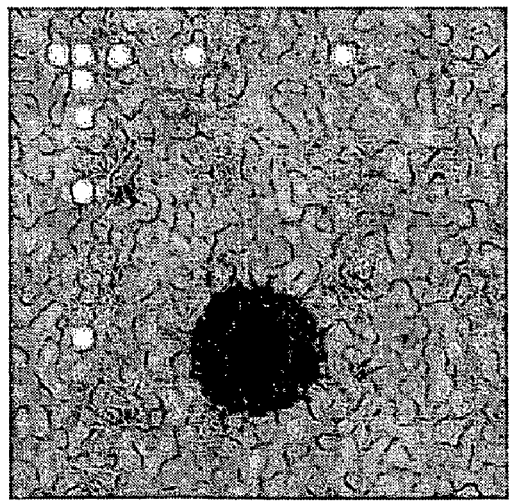
(C) 2 MHz; Real carrier
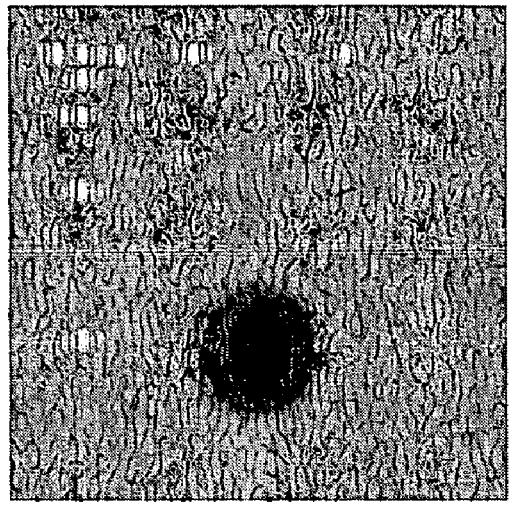
(D) 3 MHz
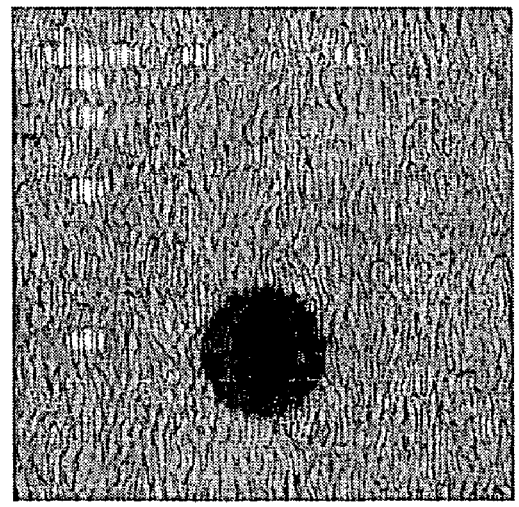

ULTRASONOGRAPHIC DEVICE AND ULTRASONOGRAPHIC METHOD

FIELD OF THE INVENTION

The present invention relates to an ultrasonic imaging device used for medical diagnosis or other purposes, and more specifically to a technique for obtaining a high quality tomographic image referred generally to as a compound scan image displayed as one image by synthesizing image signals obtained by scanning a scanned object from various angles.

DESCRIPTION OF THE RELATED ART

The ultrasonic imaging device brings an ultrasonic probe into contact with a surface of a scanned object, transmits ultrasonic waves to the object from the probe, receives reflected waves (echo signals) from the inside of the object, and displays tomographic images showing a state of various sections of the object based on the echo signals, which are used for medial diagnosis or other purposes.

FIG. 1(A) is a view illustrating the general configuration of an ultrasonic imaging device. Reference numeral 10 indicates an control unit such as a personal computer. Designated at reference numeral 11 is a CPU, at 12 a memory, at 13 a hard disk, at 21 an input device, and at 22 a display device. The devices are connected to each other through a bus 14 for delivery of various types of information between the devices. The hard disk 14 stores therein various types of programs and data required for operations of the ultrasonic imaging device, and the programs and data are read out according to the necessity and stored in the memory 12, and used for operations under control by the CPU 11. The input device is a keyboard, a mouse, or the like, and is used for receiving set-up information required by a user of the ultrasonic imaging device or for outputting operation signals. Various screens including necessary operation screens or a screen showing the results of imaging are displayed on the display device 13.

Reference numerals 23 and 24 indicate a transmitted ultrasonic beam former and a received ultrasonic beam former respectively, which are connected to the bus 14 of the control unit 10. Moreover, the transmitted beam former 23 and receiving beam former 24 are connected via a transmission/receiving-separator 31 to a ultrasonic probe 32. The transmitted beam former 23 generates an ultrasonic transmission signal corresponding to a digital signal delivered from the control unit 10 and sends the ultrasonic transmission signal via the transmission/receiving separator 31 to the ultrasonic probe 32 so that an ultrasonic signal corresponding to a program corresponding to the user's operation signal is transmitted from the ultrasonic probe 32. On the other hand, when the transmitted ultrasonic signal is received as a reflection wave from inside of the object by the ultrasonic probe 32, a signal corresponding to the received ultrasonic signal is transmitted via the transmission/receiving separator 31 to the receiving beam former 24. The receiving beam former 24 subjects the signal to required processing such as digitalization and sends the processed signal to the control unit 10. The control unit 10 processes the received signal with a program appropriate for the object of imaging, and displays a result of imaging as the display device 13.

FIG. 1(B) illustrates an example of the ultrasonic probe 32, and in this example, n sets of oscillators 1-1, 1-2, and 1-3 are arrayed in a linear state in parallel to each other. Although not shown in the figure, wiring is provided for the oscillators for transmitting a transmission signal from a transmission control circuit 23 and also a signal corresponding to a reflected wave from the inside of the object detected by each oscillator to a receiving control circuit 24. Furthermore, the ultrasonic probe 32 is an acoustic matching layer 5 made of, for instance, a mixture of metal powder and polymeric materials and an acoustic lens also made of polymeric materials for effectively bringing the oscillators into contact with the scanned object for efficient transaction of ultrasonic signals with the scanned body. By controlling amplitude of a signal given to each oscillator and timing for transmitting the signal, the focus depth, direction of irradiation and amplitude of the ultrasound irradiated from the ultrasonic probe 32 can freely be controlled, that is, the depth and direction can be controlled as indicated by $F_1$-$F_1$ and $F_2F_2$. Furthermore, to synthesize B mode image data of the object imaged from a plurality of angular directions as described below, for instance, control can be provided so that the beam is oriented to the direction A, B, or C on the focus line $F_1$-$F_1$. Although not shown in the figure, the ultrasonic probe 32 has a handle to be grasped by a user.

The configuration of the ultrasonic probe 32 is not limited to the example shown in FIG. 1(B), and for any purpose of imaging, the ultrasonic probe 32 may have various forms, for example, in which a plurality of oscillators are arranged at equal intervals in a linear, curved or planar manner. For instance, a linear scan type of ultrasonic imaging device forms an aperture by selecting a group of oscillators driving simultaneously with the preset aperture selecting function, and moves the aperture by and by to scan the inside of a sample or an object with a ultrasonic beam. Also the convex scan type of ultrasonic imaging device works similarly.

In the case of imaging only from one direction, there arise the following defects. Due to the effect of angle-dependent reflectance, only sections vertical to a direction in which the ultrasonic wave propagates within a contour of a reflecting section of the scanned object are imaged with emphasized tone, while sections of a tissue border substantially parallel to the direction in which the ultrasonic wave propagates are not images substantially at all. In addition, sections in the shadow of a highly reflective body are hardly imaged. In contrast, when there are a plurality of directions in which the ultrasonic waves propagate like in the case of compound imaging, a percentage of ultrasonic waves introduced in the vertical direction to a border surface of the reflecting body. Therefore, the contour is imaged in a relatively continuous state and is clear with the shadowed sections reduced, which contributes to the improvement of the defects described above.

A second merit is to be largely effective in removing speckles causing degradation of the contrast resolution. Since images picked up from substantially different angular directions have different speckle patterns, the signal amplitude for a section corresponding to the reflecting section of the scanned object itself increases due to the effect of addition, while the speckle patterns increase only in proportion to a root of the sum. When it is assumed that a number of added factors is N, therefore the contrast resolution is improved in proportion to a root of N.

Improvement of the contrast resolution as described above can be realized since image synthesis is carried out by converting RF signals to envelop curve signals to make the signals incoherent and then adding the signals. To describe it from the contrary viewpoint, since the signals are made incoherent and then added, improvement of spatial resolution like in the case of addition of coherent signals cannot be expected.

As a method based on the concept of addition of coherent signals, namely a method of signal synthesis in the state of RF signals, also the synthetic aperture method as disclosed in non-patent document 1 is well known in the art. In the synthetic aperture method, signals from a plurality of different angular directions are added in the coherent state, which provides the effect equivalent to enlargement of the aperture and contributes to an improvement in the spatial resolution.

In both of the compound imaging method and synthetic aperture method as described above, when the scanned object is a moving one such as a living body, movement of the body occurring between a plurality of times for imaging is troublesome. To solve the problem, in the two known examples, a method is disclosed in which positional displacement between images is estimated by means of correlation method prior to image synthesis to minimize blurring of the image due to movement of a scanned object.

[Patent Document 1]
JP-A 2002-526225

[Non-Patent Document 1]
IEEE Transaction on Ultrasonics, Ferroelectrics, and Frequency Control, Volume 45, No. 4, pp. 1077 to 1087

DISCLOSURE OF THE INVENTION

An internal organ of a human body as an object for ultrasonic imaging is not a solid body, and deforms differently from place to place. Therefore, it is difficult to perform idealistic correction for the entire image. Futhermore, influence of positional displacement between synthesized images in the synthetic aperture method is different from that in the compound imaging.

In the aperture synthesis, there occurs interference between signals to be synthesized, and if there occurs positional displacement larger than a quarter of a wavelength, the signal is degraded after synthesis. On the other hand, in the case of compound imaging, there occurs no interference between signals to be synthesized, so that positional displacement smaller than the width of an envelop of an envelop signal does not cause any signal degradation. Generally in the currently available ultrasonic imaging devices, the width of an envelop is only several times larger than the wavelength.

Since there are two image synthesis methods currently available, namely the compound imaging method and synthetic aperture method, and the two methods have different merits respectively, and there has been a desire for development of an imaging method having the merits provided by the two conventional methods as described above. In other words, the desire is to realize improvement of contrast resolution and improvement of spatial resolution at the same time and also to realize an imaging method in which an image is little degraded due to movement of a scanned object.

In the currently available ultrasonic imaging devices, a transfer function of the ultrasonic probe 32 is equivalent to a width of several waves on the time axis because the width is limited in the frequency space. In ultrasonic imaging, influence by a transfer function of the ultrasonic probe 32 occurs twice because of transmission of ultrasonic signal waves from the ultrasonic probe 32 and receiving of ultrasonic waves reflected by a scanned body with the ultrasonic probe 32, and therefore a width of the envelop is in the range from about 2 to 4 waves. In other words, influence caused by movement of a scanned object in the coherent case is around 10 times larger than that in the incoherent case. If a displacement range between synthesized images can idealistically be corrected pixel by pixel, the influence caused by movement of an scanned object could be corrected by any of the two known methods. However, since the corrected value is not always precise because of influences by noises, and there is displacement also in a direction perpendicular to the tomographic image, it is difficult to accurately estimate a local displacement.

In the present invention, it is not aimed to perfectly correct a local displacement, and correction is carried out based on the large scale displacement rate. That is to say, when a displacement is small (for instance, smaller than a quarter of a wavelength), signal synthesis is executed based on RF data, and when the displacement is larger, the signal synthesis is carried out based on the envelop detection signals. A degree of each displacement can be determined on recognition of correlation of RF data between images in different frames. Furthermore, any of signal synthesis based on RF data and signal synthesis of envelop detection signals can freely be selected by controlling a reference frequency for heterodyne detection.

BRIEF DESCRIPTION OF THE DRAWINGS

FIG. 1(A) illustrates a general configuration of a ultrasonic imaging device;

FIG. 1(B) illustrates an example of an ultrasonic probe;

FIG. 6(A) is a diagram plotted with the horizontal axis indicating a displacement between images in different frames and also with the vertical axis indicating envelop detection carried out according to the displacement and addition based on RF data;

FIG. 6(B) is a diagram illustrating an example of setup curve for setting a reference frequency $\omega_1$ for heterodyne detection;

FIG. 7 is a diagram illustrating distribution of ultrasonic wave signal intensities when the beams in three different directions A, B, and C shown in FIG. 5(B) are subjected to envelop detection to obtain the beam patterns after the envelop detection shown in FIG. 5(C) and then the signals are synthesized;

FIGS. 8(A), 8(B), 8(C), and 8(D) are diagrams illustrating examples of beam patterns showing results of heterodyne detection with the reference frequency $\omega_1$ of the reference wave set to 2 MHz, 1 MHz, 0 MHz, and −1 MHz respectively and also with the central frequency of ultrasonic wave signals $\omega_0$ set to 2 MHz;

FIG. 9(A) is a diagram showing a result of simulation for an image obtained through steps 115, 117 shown in FIG. 2;

FIG. 9(B) is a view showing a result of simulation for an image obtained through steps 119, 120 shown in FIG. 2;

FIGS. 10(A), 10(B), 10(C), and 10(D) are views showing example of images corresponding to those shown in FIGS. 8(A), 8(B), 8(C), and 8(D), respectively.

BEST MODE FOR CARRYING OUT THE INVENTION

Preferred embodiments of the present invention will be described in detail below with reference to the drawings. Each embodiment of the present invention is realized by an ultrasonic imaging device having an control unit as shown in FIGS. 1(A) and 1(B).

First Embodiment

Figure 2:
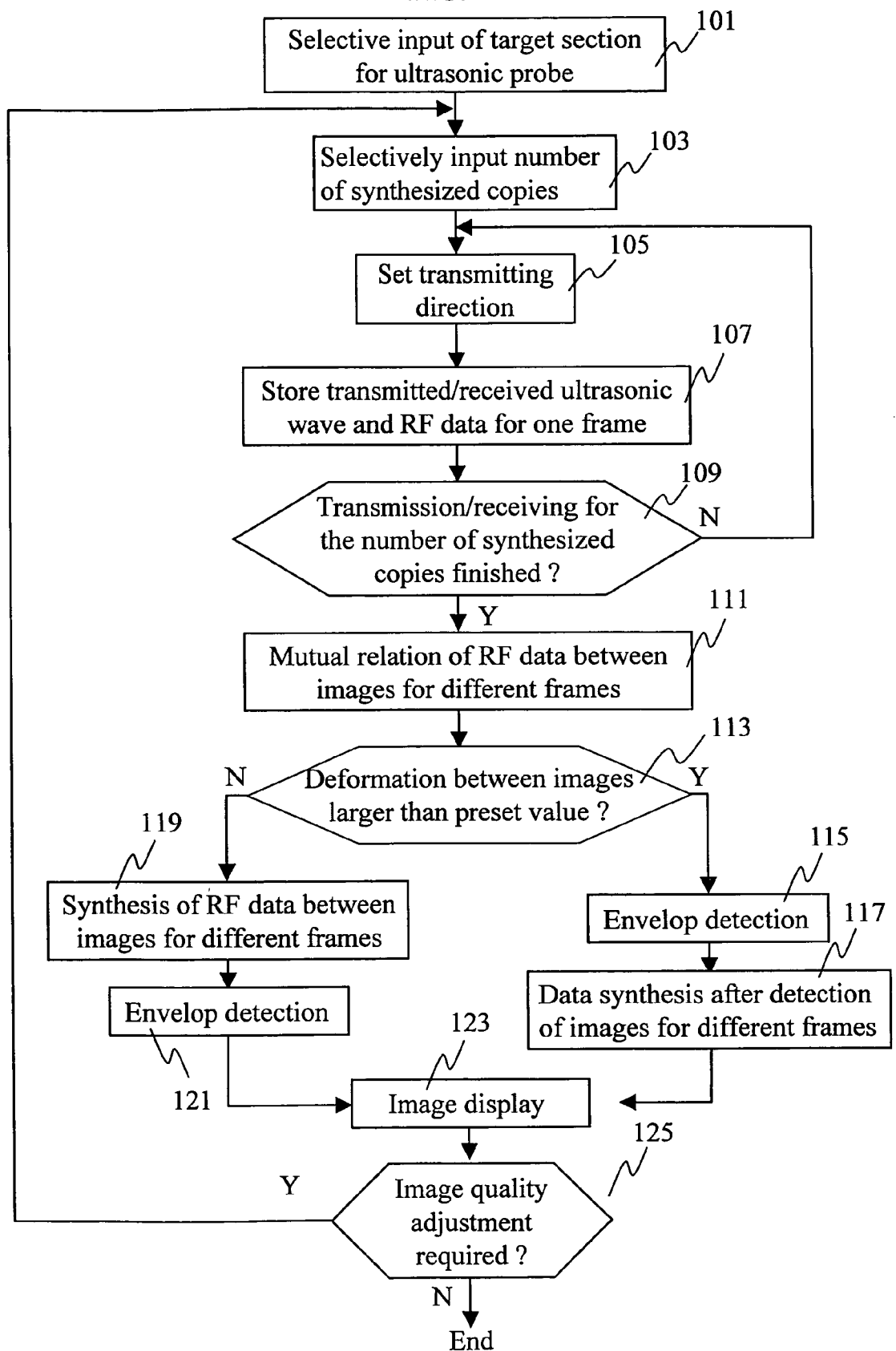
FIG. 2 is a flow chart illustrating a signal processing flow in an ultrasonic imaging device according to a first embodiment of the present invention.

FIG. 2 is a flow chart illustrating a signal processing flow in the ultrasonic imaging device according to a first embodiment of the present invention.

Reference numeral 101 indicates a preparation step, in which data such as a type of an ultrasonic probe to be used and codes indicating objective portions of an object to be imaged is inputted through an input device 21. Reference numeral 103 indicates a step of specifying the number of image frames to be synthesized for the target portions of the scanned object, in which the data is inputted through the input device 21. The number of frames to be synthesized is at least 3 or more. The number of frames may be in the range from 7 to around 15. As the number of frames to be synthesized increases, effects of image synthesis and defects caused by synthesis increase, and therefore the number of frames should preferably be determined according to an object to be imaged (movement of the object to be imaged).

Figure 5:
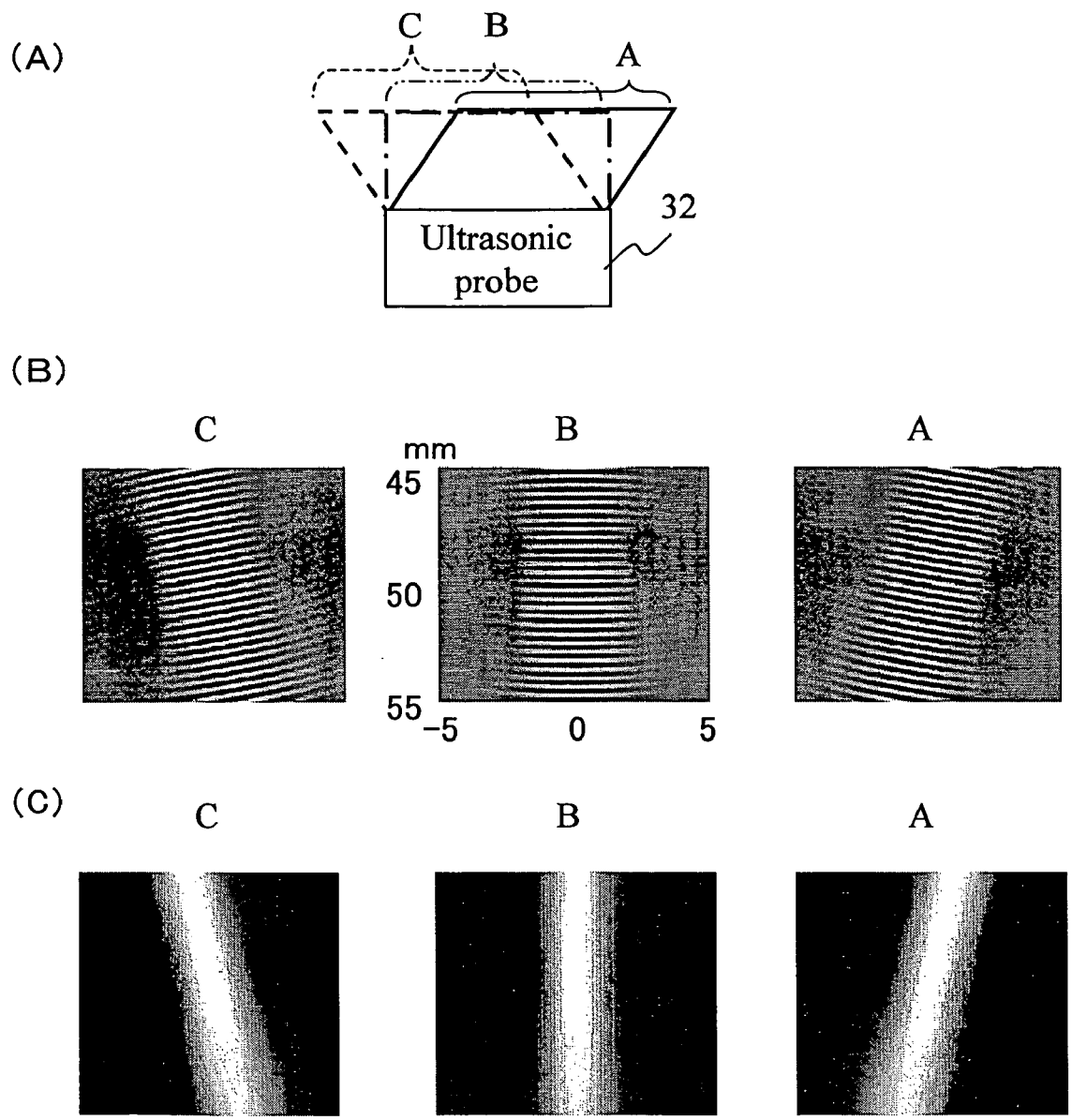
FIG. 5(A) is a schematic diagram illustrating three beam propagating directions A, B and C different from each other received by the transmitting/receiving transducer 32.
FIG. 5(B) is a diagram showing beam patterns of RF signals in the beam propagating directions received by the transmitting/receiving transducer 32.
FIG. 5(C) is a diagram illustrating beam patterns after envelop detections for RF signals received by the transmitting/receiving transducer 32.

Reference numeral 105 indicates a step for setting a direction in which ultrasonic waves are to be transmitted toward a target portion for imaging, in which the data is inputted via the input device 21. The data corresponds to the number of frames to be synthesized, specified in step 103, and the data may automatically be set by a program in response to the number of frames already imaged. Referring to FIG. 1(B), the direction of transmitting ultrasonic waves as used herein indicates each of the different directions A, B, and C transmitted on the plane of the focus $F_1$-$F_1$. In FIG. 5(A), the directions are shown as a square A schematically shown with a solid line, a square B shown with a dot and chain line, and a square C shown with a broken line. That is to say, the squares A, B, and C schematically show the state in which a scanned object is linearly scanned by transmitting ultrasonic beams at the same focus depth and at different angles.

The reference numeral 107 indicates a step of transmitting and receiving ultrasonic waves for one frame and storing RF data. When the number of imaged frames is specified (step 103) and a direction of transmitting ultrasonic waves is set (step 105), a ultrasonic wave pulse signal corresponding to a program for the target portion to be imaged is generated by the CPU 11. The signal is converted by the transmission beam former 23 to a signal given to oscillators in the ultrasonic probe 32. The converted signal is then given via the transmission/receiving separator 31 to the oscillators in the ultrasonic probe 32. The ultrasonic signal reflected from the target portion for imaging is received and converted to an electric signal by oscillators in the ultrasonic probe 32, and the electric signal is given to the receiving beam former 24 via the transmission/receiving separator 31. In the transmission/receiving separator 31, the electric signal is converted to a digital signal and subjected to phase-aligned addition between channels, and is stored as RF data in the memory 12. Reference numeral 109 indicates a step of evaluating the number of frames already imaged, in which a check is made as to whether or not RF data for transmitted/received signals has been stored by the number of frames specified in step 103. When it is determined that RF data has not been stored by the number of frames specified in step 103, the processing returns to step 105, in which the RF data for transmitted and received ultrasonic signals for one frame in the next signal transmitting direction is stored. When it is determined in step 108 that the number of frames already imaged has been stored by the number specified in step 103, the processing proceeds to data assessment.

Reference numeral 111 indicates a step of computing correlation of RF data between images for different frames. In this step, image data for the respective frames stored in the memory 12 are sequentially read out to compute the correlation. In other words, an amount of displacement and an amount of deformation are computed by especially checking a specified reflecting portion of a scanned object in each ultrasonic wave transmitting direction on the basis of image data for each frame.

Reference numeral 113 indicates a step of checking whether or not a deformation rate between images for different frames is greater than a preset value. That is to say, when it is determined that the correlation of RF data between images for different frames computed in step 111 is greater than the preset value, the RF data for each frame stored in the memory 12 is subjected to envelop detection (step 115), and data synthesis is carried out between images of the different frames based on the data after the envelop detection (step 117). When the correlation value of RF data between images for different frames is smaller than the preset value, data synthesis is carried out between images for different frames based on the RF data for each frame stored in the memory 12 (step 121), and the synthesized RF data is subjected to envelop detection (step S121).

Reference numeral 123 indicates an image display step, in which an image satisfying requirements of a particular program is displayed on the display device 22 based on either one of the data obtained in step 117 or data in step 121. Reference numeral 125 indicates a step of determining whether or not adjustment of the image quality is required. For instance, in the image display step 123, the question of "data re-acquisition required?" and "YES", "NO" switches are displayed at a portion of the screen. When the user is not satisfied with the image displayed on the display device 22 and selects "YES", the processing returns to step 103, and the processing flow is again executed from the necessary setup process. When the user selects "NO", imaging is finished. When imaging is to be carried out again, the conditions for acquiring RF data of transmitted and received ultrasonic signals are changed, for instance, by increasing the number of synthesized images, or by making a change rate of a signal transmitting direction minuter. In the ultrasonic diagnostic unit, imaging is continued and the screen is continuously updated unless the imaging stop button is pressed. Because of the feature, even when a screen display of inquiring the necessity of data acquisition is not provided, the user can change the setup according to each image or reflect the changed conditions to imaging next time.

As described above, influence of displacement of target portions included in a scanned object over synthesized signals largely varies between a case of coherent signals such as RF signals and a case of incoherent signals such as envelop detection signals. In the case of coherent signals, when the displacement is equal to a half of the wavelength or more, the signals cancel each other completely, and the influence can be ignored only when the displacement is not greater than a quarter of the wavelength. In the case of coherent signals, canceling never occurs, and therefore the influence is small when the displacement is not greater than a width of the envelop.

In the first embodiment of the present invention, in recognition of the point described above, correlation of RF data between images for different frames is computed in step 111, and whether a deformation between images for different frames is larger than a preset value or not is determined in step 113. When a displacement of a target position of a scanned object between images for different frames is larger than the preset value, the signal processing is carried out based on incoherent signals giving smaller influence due to displacement between images for different frames. When displacement of a target position of a scanned object between images for different frames is smaller than the preset value, the signal processing is carried out based on coherent signals.

A method of computing a deformation based on correlation is described in detail below. In the following descriptions, symbol M indicates the number of data in the depth direction in one frame, and N indicates the number of data in the horizontal direction. Further, it is assumed in the following descriptions that the coordinate values for the depth direction become larger from the shallower positions to the deeper positions, and the coordinate values along the horizontal axis become larger according to a sequential order of a scanned luster. It is also assumed in the following directions that scanning is carried out sequentially in the horizontal direction. In the following descriptions, $I^k_{i,j}$ indicates brightness of a pixel located at the i-th position in the depth direction and j-th position in the horizontal direction in the frame number k, and $A^k_{i,j}$ indicates an amplitude of an RF signal at the same position.

Assuming that w indicates a size of a window for which correlation is to be computed, the deformation vector $V^k_{i,j}$ based on correlation between two frames at the pixel ij is computed through equations (1) and (2) below. The correlation Cr(k, K+1) is computed through equation (1) below:

$$C_r(k, k+1) = \left(A^k_{i-\frac{w-1}{2},j} \cdots A^k_{i+\frac{w-1}{2},j}\right) * \left(A^{k+1}_{i-\frac{w-1}{2},j} \cdots A^{k+1}_{i+\frac{w-1}{2},j}\right) \quad (1)$$

$$C_r(k, k) = \left(A^k_{i-\frac{w-1}{2},j} \cdots A^k_{i+\frac{w-1}{2},j}\right) * \left(A^k_{i-\frac{w-1}{2},j} \cdots A^k_{i+\frac{w-1}{2},j}\right) \quad (2)$$

On the other hand the self correlation Cr(k, k) is computed through equation (2) above.

The difference between the pixel number imax1 where the correlation Cr (k, K+1) is maximized and the pixel number imax0 where the self correlation cr (k, k) (V=imax0−imax1) indicates a deformation in the depth direction between a frame k and frame k+1. In the equations above symbol * indicates correlation. In the above descriptions, it is assumed that w is an odd number, but also when w is an even number, computing can be executed similarly by replacing i−(w−1)/2 with i−(w−2)/2 and i+(w−1)/2 with i+w/2.

In the descriptions above, a local deformation is treated as a one-dimensional program only in the depth direction although the local deformation relates to a two-dimensional vector. The reason is that, because point responses based on transmitted and received ultrasonic pulses are distributed in a narrow area along the depth direction and in a wide direction along the azimuth direction, sampling is executed more finely as compared to the Nyquist frequency of the RF signal wave along the depth direction and more roughly along the azimuth direction. When compared quantitatively, in a case where the sonic velocity is 1500 m/s and the sampling frequency in the depth direction is 50 MHz, the sampling interval in the depth direction is 15 μm. On the other hand, the sampling interval in the azimuth direction is generally equivalent to the element pitch or around a half of the element pitch. Therefore, assuming that the element width is around a half of the central frequency, when the central frequency is 3 MHz, the sampling pitch is around 125 μm, which is about 10 times larger than that in the depth direction. Because of it, when the frame rate is fully higher as compared with a velocity of the scanned object, the deformation may be measured only in the depth direction.

A window is set for computing correlation for the following two reasons. The first reason is that, when all of data for one luster is used out all at once, it is disadvantageous for scanning an object such as a living thing which can not be treated as a solid object, because the deformation varies according to the depth. Secondly, in the present invention, correlation is computed between images picked up from different angular directions, and therefore, when a luster is compared to another luster, places can not be matched with each other in the depth direction. However, when a limit is introduced for a window width, it is possible to prevent a luster from being overlapped on another luster within a range of the window. For instance, when a deformation is computed between frames imaged from beam directions different by 5 degrees from each other, if the luster interval is 125 μm and the sampling interval in he depth direction is 15 μm, 125 μm/tan (5 degrees)/15 μm=95, and therefore when the window width is not more than 95 sampling points, it can be recognized that also the deformation in the azimuth direction is computed based on data acquired at the same position. Needless to say, in this case, the number of a luster as a partner for correlation changes in association with movement of the window.

After a deformation at the pixel ij is computed as described above, when influence by noises is small, the obtained data may be used as a deformation rate as it is. When the influence by noises is large, however, it is also possible to execute the processing by replacing the value with an average value with, for instance, a low-pass spatial filter.

When movement of a scanned object is faster as compared to the frame rate, the two-dimensional deformation may be computed by computing a two-dimensional deformation based on the two-dimensional correlation including the azimuth direction, or by integrating the values luster by luster in the depth direction, computing the deformation in the azimuth direction based on correlation of integrated patterns for different frames, and combining the deformation with that in the depth direction described before.

FIG. 6(A) is a diagram plotted with a displacement between images for frames along the horizontal axis and selection between addition of RF data and envelop detection executed according to the displacement along the vertical axis. In this example, the threshold value for a displacement between images for different frames is a quarter of a wavelength of the ultrasonic wave with the central frequency $\omega_0$. When the displacement between images for different frames is larger than a quarter of the wavelength of the ultrasonic wave with the central frequency $\omega_0$, the signal processing is executed by envelop detection, namely based on the incoherent signals. When the displacement between images for different frames is smaller than a quarter of the wavelength of the ultrasonic wave with the central frequency $\omega_0$, the signal processing is carried out by executing addition based on the RF data and then by envelop detection, namely based on the coherent signals.

As described above, by selecting signals for image generation in response to a displacement of target portions to be imaged between images for different frames, it is possible to realize the improvements of the contrast resolution and the spatial resolution at the same time for providing an imaging method with low image degradation due to movement of a scanned object.

Second Embodiment

Figure 3:
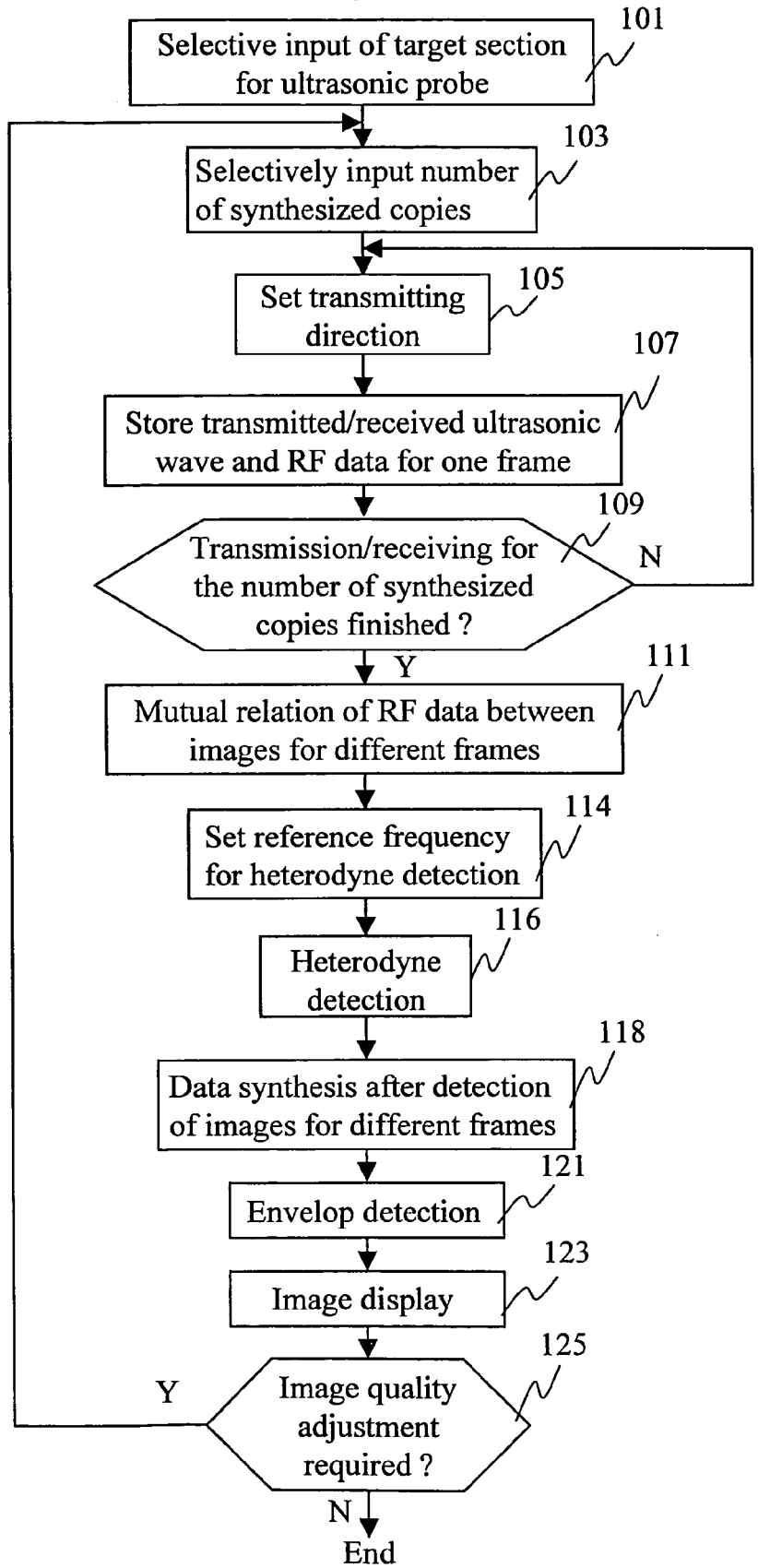
FIG. 3 is a flow chart illustrating a signal processing flow in an ultrasonic imaging device according to a second embodiment of the present invention.

FIG. 3 is a flow chart illustrating a signal processing flow in an ultrasonic imaging device according to a second embodiment of the present invention. In FIG. 3, the same reference numbers are assigned to the corresponding steps in FIG. 2.

Also in the second embodiment, like in the first embodiment, a type of a ultrasonic probe to be used and a target portion of a scanned object are set (step 101), the number of frames to be imaged for image synthesis is specified (step 103), a ultrasonic signal wave transmission direction toward each target portion to be imaged is set (step 105), RF data for transmitted and received ultrasonic signal waves for one frame is stored (step 107), the number of imaged frames is checked (step 109), and the processing sequence is repeated until the number of imaged frames reaches the number of frames specified in step 103. Then correlation of RF data between images for different frames in step 111 is computed.

Reference numeral 114 indicates a step of setting the reference frequency $\omega_1$ for heterodyne detection, and reference numeral 116 indicates a step of executing the heterodyne direction corresponding to the set reference frequency $\omega_1$. Reference numeral 118 indicates a step of receiving a result of detection in step 116 and synthesizing data after detection of images for different frames. The image display in step 123 and image quality adjustment in step 125 are the same as those described in the first embodiment.

FIG. 6(B) illustrates an example of setup curve for setting the reference frequency $\omega_1$ for heterodyne detection in step 114. This diagram is plotted with the horizontal axis indicating a displacement between images for different frames with respect to a wavelength of ultrasonic wave with the central frequency $\omega_0$ of the ultrasonic wave and also with the vertical axis indicating a ratio of a frequency after mixing corresponding to the reference frequency determined in response to each displacement to the central frequency $\omega_0$ of the ultrasonic wave. Also in the second embodiment, like in the first embodiment, a quarter of a wavelength of ultrasonic wave with the central frequency $\omega_0$ is used as a threshold value for the displacement between images for different frames. In other words, when the displacement between images for different frames is a quarter of the wavelength of ultrasonic wave with the central frequency $\omega_0$, the reference frequency for heterodyne detection is the same as the central frequency $\omega_0$ of the ultrasonic wave. When the displacement between images for different frames is different from a quarter of the wavelength of ultrasonic wave with the central frequency $\omega_0$, the reference frequency is set to the frequency after mixing shown in FIG. 6(B). As a result, only when the displacement between images for different frames is equal to a quarter of the wavelength of ultrasonic wave with the central frequency $\omega_0$, the signal processing is carried out by envelop detection, namely based on the incoherent signals. On the other hand, when the displacement between images for different frames is different from a quarter of the wavelength of ultrasonic wave with the central frequency $\omega_0$, the reference frequency is selected according to the degree of difference. In addition, heterodyne detection based on the RF data is carried out, and then the signal processing is executed by envelop detection, namely based on the coherent signals.

In the second embodiment, only when the correlation of RF data between images for different frames computed in step 111 is equal to a prespecified threshold value, the reference frequency $\omega_1$ is set to a value equal to the central frequency $\omega_0$ of the ultrasonic wave to execute homodyne detection. In other words, RF data for the transmitted and received ultrasonic waves is treated as coherent signals, and imaging is carried out by envelop detection. When the correlation of RF data between images for different frames is different from the threshold value, the reference frequency $\omega_1$ is set to a value different from the central frequency $\omega_0$ of the ultrasonic wave to execute heterodyne detection.

The method of executing switching between coherent signals and incoherent signals by means of heterodyne detection in the second embodiment is described in more details below.

FIG. 5(A) is a schematic diagram illustrating three beam propagating directions A, B and C different from each other received by the transmitting/receiving transducer 32. FIG. 5(B) is a diagram showing beam patterns of RF signals in the beam propagating directions received by the transmitting/receiving transducer 32. FIG. 5(C) is a diagram illustrating beam patterns after envelop detections for RF signals received by the transmitting/receiving transducer 32. As clearly understood when FIG. 5(B) is compared to FIG. 5(C), only the intensity signals are strongly displayed and the phase signals are hard to be recognized visually in the beam patterns after envelop detection.

FIG. 7 illustrates distribution of ultrasonic signal intensities after beam patterns are obtained by executing envelop detection for the beams in the different three directions A, B, and C as shown in FIG. 5(B) and then synthesizing the beam patterns shown in FIG. 5(C). That is, the horizontal direction indicates a spread of ultrasonic signal waves, and the vertical direction indicates the focus depth. FIG. 7 illustrates a case in which the transmitting/receiving transducer 32 is focused to a position with the depth of 50 mm and the spread is ±2 degrees at the focus position. The lines extending along the vertical axis indicate a contour of ultrasonic signal intensities.

The RF signal as shown in FIG. 5(B) can be expressed as a time function F(t) by equation (3) below:

$$F(t)=A(t)\sin(\omega_0) \qquad (3)$$

wherein $\omega_0$ indicates a central frequency of the ultrasonic wave signal, and A(t) indicates the envelop.

There is the homodyne detection as a specific variant of the heterodyne detection for detecting the envelop expressed by F(t).

Assuming that G(t) indicates a signal obtained by multiplying F(t) by the reference wave sin ($\omega_1$t), the following equation is obtained:

$$G(t)=(\tfrac{1}{2})A(t)[\sin\{(\omega_0-\omega_1)t\}+\sin\{(\omega_0+\omega_1)t\}] \qquad (4)$$

Assuming that the frequency $\omega_1$ of the reference wave is equal to the central frequency $\omega_0$ of the ultrasonic signal, when the homodyne detection is executed, the following equation is obtained:

$$G(t)=(\tfrac{1}{2})A(t)2\sin(2\omega_0 t) \qquad (5)$$

and therefore, by removing the double harmonic component with the low band pass filter, an envelop signal can be obtained.

In other words, by executing the homodyne detection as a particular variant of the heterodyne detection executed with the reference signal wave $\sin(\omega_0 t)$ with the frequency which is equal to the central frequency $\omega_0$ of the ultrasonic signal, image synthesis can be executed with the incoherent signals obtained after the envelop detection described in the first embodiment. Specifically, as shown in FIG. 6(B), image synthesis is executed based on the RF signals, namely coherent signals only when a displacement between images for different frames is a specific value (a quarter of a wavelength of the ultrasonic signal with the central frequency in the figure). When the displacement is different from the specific value, the reference frequency $\omega_1$ after heterodyne detection is set to a value different from the central frequency $\omega_0$ of the ultrasonic signal as shown in the figure based on the correlation between RF data as a parameter. With this operation, the coherent signals can be changed successively to incoherent signals, and image synthesis based on both the incoherent signals and coherent signals can be realized.

FIG. 8 illustrates how the distribution of ultrasonic wave intensities shown in FIG. 7 changes with reference to the cases in which the central frequency $\omega_0$ of ultrasonic wave is set to 2 MHz and the frequency $\omega_1$ of the reference wave is set to 2 MHz, 1 MHz, 0 MHz, and –1 MHz.

FIG. 8(A), FIG. 8(B), FIG. 8(C), and FIG. 8(D) shows examples of beam patterns indicating the results of heterodyne detection when the frequency $\omega_1$ of the reference wave is set to 2 MHz, 1 MHz, 0 MHz, and –1 MHz. As the beam pattern is thinner (with small spread), the spatial resolution in the azimuth direction is higher, and as the side lobe is stronger, speckle patterns are generated more strongly with the contrast resolution degraded.

FIG. 8(A) shows a case where the frequency $\omega_1$ of the reference wave is 2 MHz, that is, the frequency after mixing with the reference wave and passing through the low pass filter (a frequency after heterodyne detection) is 0 MHz, and this case corresponds to the envelop detection described in relation to step 115 in the first embodiment. In this example, the contrast resolution is the highest, and the spatial resolution is the lowest. FIG. 8(C) shows a case where the frequency $\omega_1$ of the reference wave is 0 MHz, that is, the frequency after the frequency after heterodyne detection is 2 MHz, and therefore this case corresponds to detection of received RF signals, in other words to the envelop detection after synthesis of RF data in step 119 in the first embodiment. FIG. 8(B) shows a case where the frequency $\omega_1$ of the reference wave is 1 MHz, that is, the frequency after heterodyne detection is 0 MHz, and therefore an intermediate state between those shown in FIGS. 8(A) and 8(C) is obtained. FIG. 8(D) shows a case where the frequency $\omega_1$ of the reference wave is –1 MHz, that is, the frequency after heterodyne detection is 3 MHz (the reference wave has a phase reverse to that shown in FIG. 8(B)), and in this case, the spatial resolution is highest, and the contrast resolution is low.

In other words, it can be understood also from the forms of the beam patterns that coherent signals can successively be changed to incoherent signals, and FIGS. 9 and 10 show examples of screens displaying the image after synthesis.

FIG. 9(A) shows an example of a result of simulation for an image obtained through steps 115 and 117 shown in FIG. 2, while FIG. 9(B) shows an example of a result of simulation for an image obtained through steps 119 and 120 shown in FIG. 2. This case shows an example of a result of simulation for imaging a portion of a human body in which a blood vessel not reflecting ultrasonic waves is present with the size of 5 cm×5 cm. A black portion at a central lower section corresponds to the blood vessel, while the peripheral portion corresponds to the body. White dots on the left side and in the upper edge section are images of dot-like reflecting bodies. As understood from comparison of FIG. 9(A) to FIG. 9(B), the image obtained by synthesis in the state of RF signals in FIG. 9(B) shows the higher spatial resolution.

FIGS. 10(A) to 10(D) show examples of images corresponding to those shown in FIGS. 8(A) to (D), respectively, which are results of simulation executed in the same way as shown in FIGS. 9(A) and 9(B). FIG. 10(A) shows a case in which the frequency $\omega_1$ of the reference wave is 2 MHz as with the case shown in FIG. 9(A) corresponding to the envelop detection described above. FIG. 10(C) shows a case in which the frequency $\omega_1$ of the reference wave is 0 MHz, and this case corresponds to detection of received RF signal which is the same as the envelop detection shown in FIG. 9(B) after synthesis of RF data in step 119 in the first embodiment. FIG. 10(B) shows case in which, as with the case shown in FIG. 8(B), the frequency $\omega_1$ of the reference wave is 1 MHz, and therefore a result indicating an intermediate state between those shown in FIGS. 10(A) and 10(C) is obtained. FIG. 10(D) shows a case in which, as with the case shown in FIG. 8(D), the frequency $\omega_1$ of the reference wave is –1 MHz (the reference wave has a phase reverse to that shown in FIG. 7(B)), and therefore the spatial resolution is the most excellent, while the contrast resolution is low.

Third Embodiment

Figure 4:
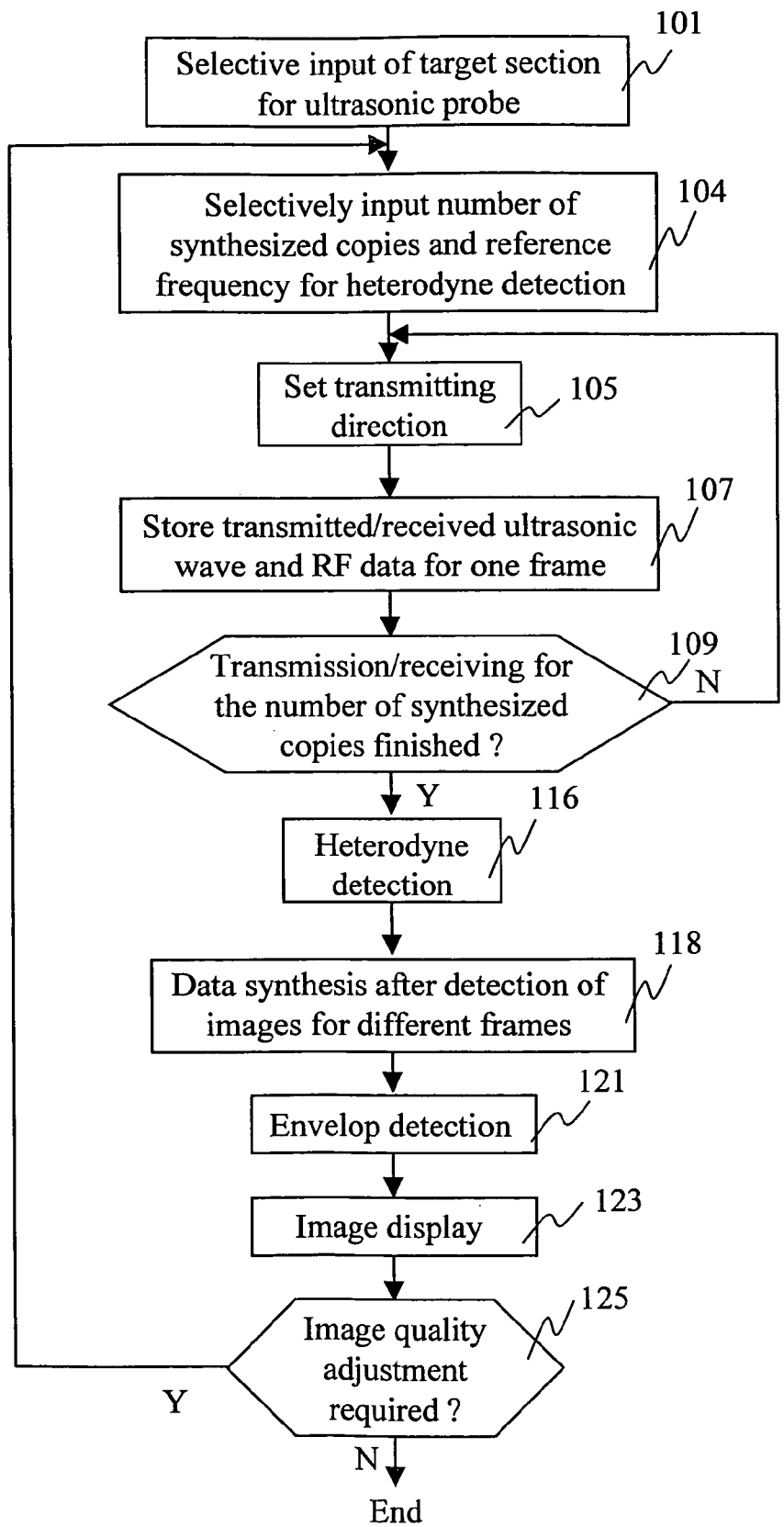
FIG. 4 is a flow chart illustrating a signal processing flow in an ultrasonic imaging device according to a third embodiment of the present invention.

FIG. 4 is a flow chart illustrating a signal processing flow in an ultrasonic imaging device according to a third embodiment of the present invention. In FIG. 4, the same reference numerals are assigned to the steps of executing the same processing steps shown in FIG. 2 or 3.

In the second embodiment, a reference frequency for heterodyne detection is automatically selected according to correlation of RF data between images for different frames (step 114). In the third embodiment, however, a user can change the reference frequency for heterodyne detection based on the user's policy in step 104, which is the only difference from the second embodiment. Other processing steps are the same as those shown in the processing flow shown in FIG. 3.

Figure 11:
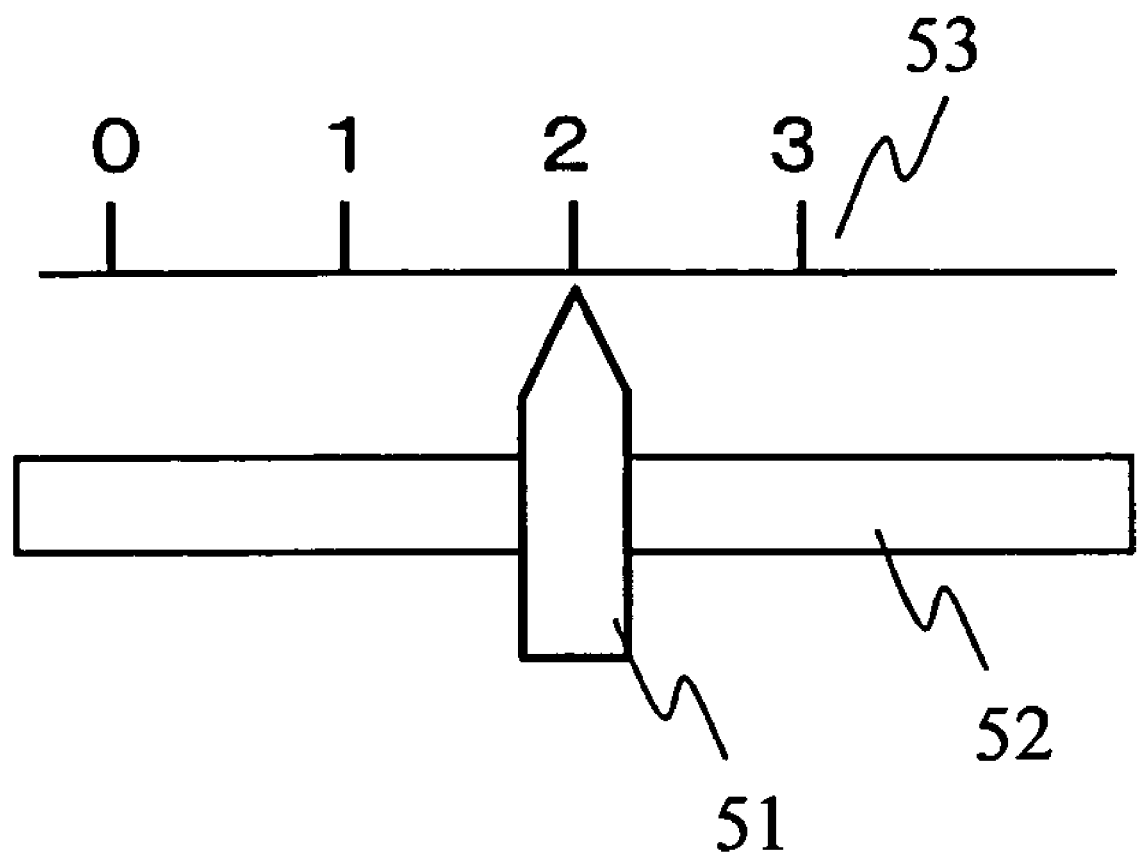
FIG. 11 illustrates an appearance of an input device operated by a user to set a frequency of a reference wave in the ultrasonic imaging device according to the third embodiment of the present invention.

FIG. 11 shows an appearance of an input device operated by a user in step 104 in the third embodiment. Reference numeral 51 indicates an operation button, which can be moved in the horizontal direction along a travel guide 52. Reference numeral 53 indicates a display section. In this example, a volume type of operation button which can linearly be moved is shown. For instance, the displays 0-3 indicate positions for specifying the reference frequencies for obtaining images corresponding to FIGS. 10 (A) to (D), respectively. In other words, operation of the operation button 51 indicates setting of the reference frequency $\omega_1$ for heterodyne detection corresponding to FIG. 6(B). In this case, the user can accumulate knowledge as to how the obtained image changes according to an object or a disease to be checked through experiences, so that the user can determine which of the contrast resolution and spatial resolution should come first case by case.

In the descriptions above, the number of images to be synthesized is three, but the number may be made larger. In this case, it is possible to synthesize a coherent image using a portion of the images and synthesize an incoherent image using the remaining images, and also to obtain an image by mixing the coherent and incoherent images.

The present invention is not limited to the embodiments described above, and various deformations are allowable within a range of the technical idea.

The present invention enables an improvement in spatial resolution by synthesis when an object for scanning moves only a little, and also enables an improvement in contrast resolution even when the object largely moves. In other words, the present invention makes it possible to obtain an image with a good balance between the contrast resolution and spatial resolution according to a positional displacement between images to be synthesized. Further the present invention makes it possible to acquire an image with a good balance between the contrast resolution and spatial resolution according to an object to be imaged, or according to selection by the user.

What is claimed is:

1. An ultrasonic imaging device comprising:
   a control unit which sends ultrasonic pulse signals for forming an ultrasonic beam to be given to a scanned object and receives a received ultrasonic beam formed from the ultrasonic pulse signals reflected from the scanned object;
   a transmitted ultrasonic beam former which forms a transmitted ultrasonic beam in response to the ultrasonic pulse signals;
   an ultrasonic probe which receives an output from the transmitted ultrasonic beam former via a transmission/receiving separator and sends the transmitted ultrasonic beam to the scanned body; and
   a receiving beam former which receives the ultrasonic pulse signals reflected by the scanned object received with the ultrasonic probe via the transmission/receiving separator and forms the received ultrasonic beam;
   wherein the control unit has a program for synthesizing B-mode image data of the scanned object imaged from a plurality of angular directions against the scanned object and displaying the synthesized image, the control unit computing correlation between the received ultrasonic beams for frames imaged from the plurality of angular directions, selecting a reference frequency for detection for the received ultrasonic beam according to a result of the computation of the correlation, and setting the reference frequency to a value equal to a central frequency of the ultrasonic pulse signals when the correlation value is equal to a prespecified value.

* * * * *